(12) United States Patent
Chan

(10) Patent No.: US 6,472,503 B2
(45) Date of Patent: Oct. 29, 2002

(54) METHOD FOR DRYING ELECTROPHORESIS GELS

(75) Inventor: Grace Y. Chan, North Ryde (AU)

(73) Assignee: Gradipore Limited, Frenchs Forest (AU)

( * ) Notice: Subject to any disclaimer, the term of this patent is extended or adjusted under 35 U.S.C. 154(b) by 0 days.

(21) Appl. No.: 09/956,389

(22) Filed: Sep. 19, 2001

(65) Prior Publication Data

US 2002/0038520 A1 Apr. 4, 2002

Related U.S. Application Data

(63) Continuation of application No. 09/476,574, filed on Jan. 3, 2000, now abandoned.

(51) Int. Cl.⁷ .................................................. C08F 6/00
(52) U.S. Cl. ..................................................... 528/480
(58) Field of Search .......................................... 528/480

(56) References Cited

FOREIGN PATENT DOCUMENTS

| DE | 3935020 | 4/1991 |
|---|---|---|
| EP | 225403 | 6/1987 |
| EP | 758747 | 2/1997 |
| WO | WO 9719989 | 6/1997 |

Primary Examiner—Terressa M. Boykin
(74) Attorney, Agent, or Firm—Baker & McKenzie

(57) ABSTRACT

A method for drying a polyacrylamide gel, the method comprising contacting the gel with an aqueous solution of a polyhydoxy alcohol other than a polyhydroxy alcohol having at least 3 vicinal hydroxy groups and drying the gel. Examples of suitable polyhydroxy alcohols include 1,2-ethane diol, 1,2-propane diol, 1,3-propane diol, 1,4-butane diol, 1,6 hexane diol, alkyl triol, 1,2,6-trihydroxy hexane, trimethylol propane and pentaerythritol. The gel may be dried between two cellophane sheets positioned in a drying frame arrangement.

17 Claims, 4 Drawing Sheets

Fig. 2
2(c)
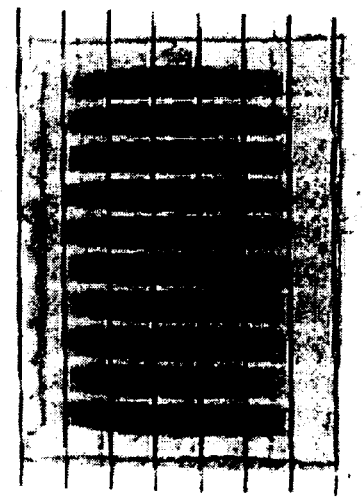
2(f)
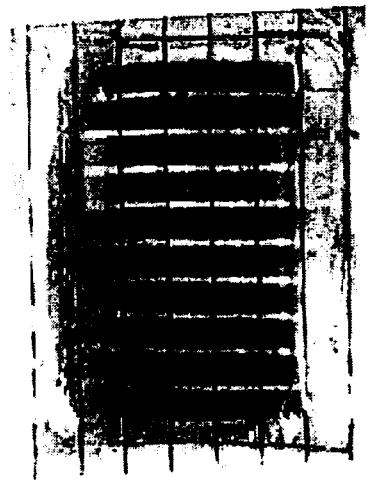
2(b)
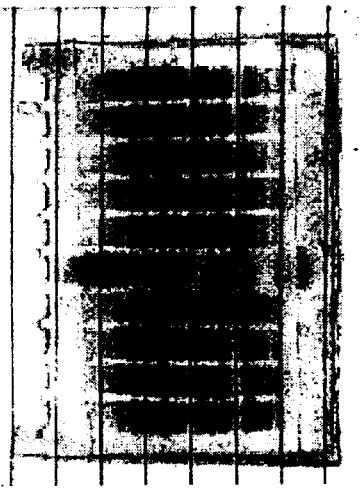
2(e)
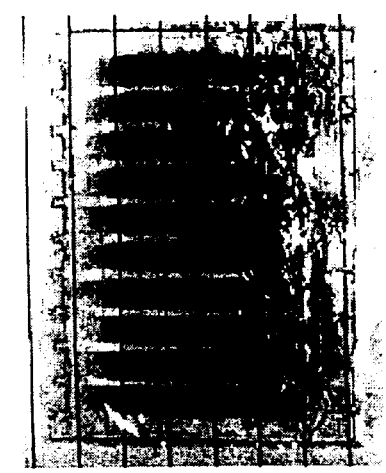
2(a)
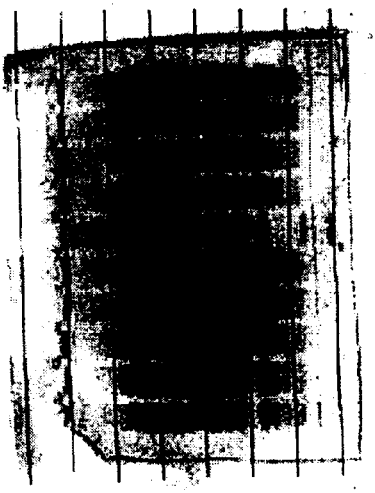
2(d)

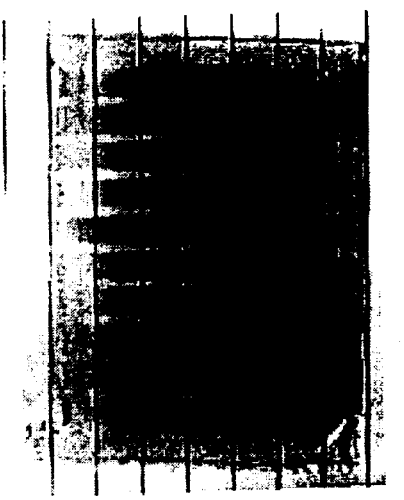
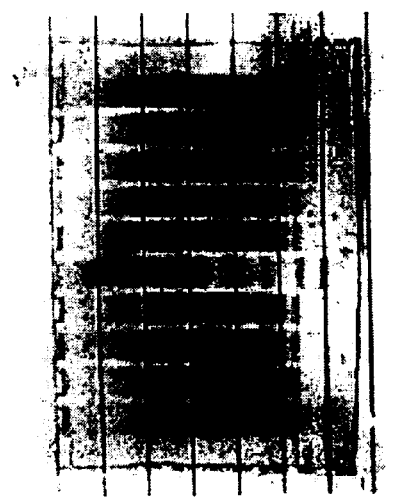
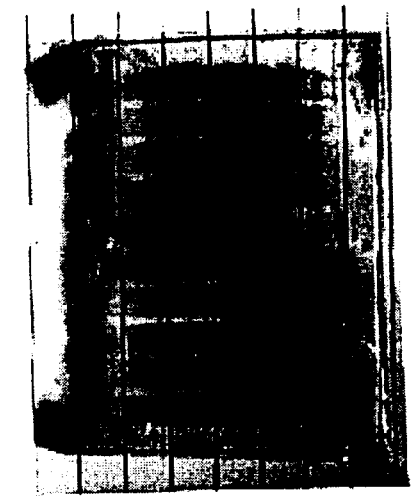
Fig. 2 (contd.)

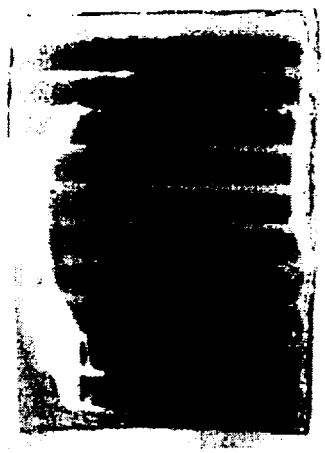
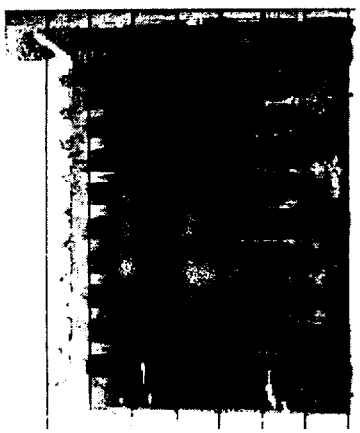
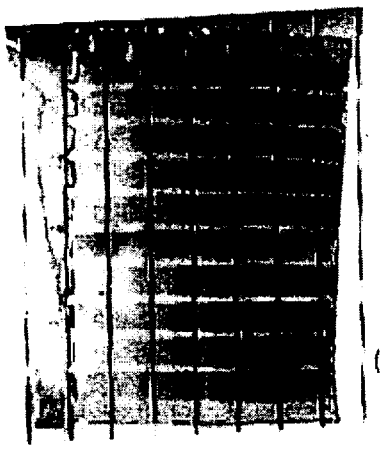
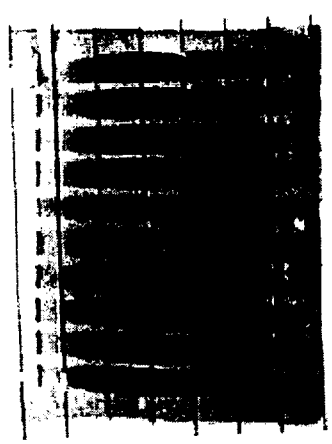
Fig. 3(a)  Fig. 3(b)  Fig. 3(c)  Fig. 3(d)
Fig. 3
Fig. 4

METHOD FOR DRYING ELECTROPHORESIS GELS

CROSS REFERENCE TO PARENT APPLICAITON

This application is a continuation application of U.S. patent application having Ser. No. 09/476,574 filed on Jan. 3, 2000 now abandoned.

BACKGROUND OF THE INVENTION

1. Field of the Invention

The present invention relates to a method for drying electrophoresis gels and in particular is concerned with compositions and methods for drying polyacrylamide gels.

2. Background Art

Gel electrophoresis is a technique much used to separate biological macromolecules such as polypeptides, proteins, DNA and RNA. Polyacrylamide is one commonly used gel forming polymer.

In polyacrylamide gel electrophoresis, a polyacrylamide gel containing an appropriate buffer is cast into a thin slab between glass or plastic plates or enclosed in a glass tube. The slab is placed between electrode compartments and a small amount of a solution of the sample is pipetted into precast notches on the top of the gel. Usually a water soluble cationic or anionic tracking dye is added. The dye migrates faster than the macroions so that the progress of the experiment can be tracked. The current is turned on and run until the tracking dye band is near the bottom of the slab. The gel is then removed and generally stained with a dye that binds to the proteins or nucleic acids.

The gel cannot be stored for a prolonged period as it becomes brittle or swells excessively if left as is. Therefore, in many cases, profiles of electrophoresis gels are photographed or copied on paper or the like and stored as images.

However, in photographing or copying the gel it is difficult to accurately record thin bands or very subtle differences in density of stains. In addition, biological macromolecules which have been separated by electrophoresis cannot be recovered. In order to mitigate this problem various proposals for drying the gel for storage have been proposed.

U.S. Pat. No. 5,635,046 (Daiichi Pure Chemicals Co., Ltd.), the disclosure of which is incorporated herein by reference, describes prior art methods for drying gels.

One such method is dislosed in U.S. Pat. No. 4,883,597, the disclosure of which is also incorporated herein by reference. The patent describes a drying method in which water vapour is extracted from a gel supported by a polyethylene membrane by apply a vacuum through the membrane.

Other more complex methods involve drying devices utilizing both heat and vacuum sources in attempt to uniformly remove moisture from the gel. Such a procedure commonly involves positioning the gel matrix on a filter paper and placing the resulting combination of gel matrix on filter paper within a drying apparatus in which the combination is subjected to a vacuum source and heated to remove liquid from the gel. An example of such an arrangement is shown in U.S. Pat. No. 4,020,563. Similarly, U.S. Pat. Nos. 4,612,710 and 4,788,778 disclose a method and apparatus in which heat is provided to a horizontal gel slab from a heating plate below while drawing a vacuum beneath.

However, as pointed out in U.S. Pat. No. 5,635,046, a method in which gels are dried with heat under reduced pressure requires a dedicated drying apparatus and a vacuum pump, which are both relatively expensive. In addition, when gels contain acrylamides at high concentrations of not less than 15% by weight, frequently the gels are damaged due to cracking. Moreover, methods using an organic solvent to dewater gels tend to result in a loss in transparency or deformation of the gel, raising a problem in recording images accurately.

An alternative method for drying gels is to sandwich the gel between cellophane films (for example, extruded cellulose xanthate) or the like. An advantage of this method is that it does not require special equipment, apart from the optional use of a simple drying frame. Moreover, sandwiching the gel between two cellophane films has the further advantage of suppressing deformation of the gel during the drying process.

However, even when the cellophane sandwich method is used, cracking of the gel can occur, especially when using gels containing polyacrylamides at high concentrations of not less than 15% by weight.

Furthermore, the gels can lose transparency, particularly at low gel concentrations.

To avoid this problem, a number of methods have been proposed including incorporation of glycerol in the gel and application of gelatin or a paste onto the surface of a gel. However, these methods remain ineffective for preventing the occurrence of cracks in the case of gels having high concentrations of acrylamide.

SUMMARY OF THE INVENTION

The present inventor has found that the use of polyhydroxy alcohols in the drying process gives transparent gels that do not experience significant cracking during the dry process, even where the gels have high or low concentrations of polyacrylamide. This is a surprising outcome give that the use of glycerol, a polyol, results in significant cracking of the gel during the drying process.

Without wishing to limit the present invention in any way, it is believed that the gel cracking resulting from the use of glycerol in the drying process is in some way related to the vicinal nature of three hydroxy groups of glycerol (1,2,3 propane triol). The inventor has found that cracking of the gel during the drying process can be avoided provided that the polyhydroxy alcohol used has no vicinal hydroxy groups, or if it does have vicinal hydroxy groups, it has no more that 2 vicinal hydroxy groups.

Accordingly, the present invention provides a method for drying a polyacrylamide gel, the method comprising contacting the gel with au aqueous solution of a polyhydroxy alcohol other than a polyhydroxy alcohol having at least 3 vicinal hydroxy groups and drying the gel.

The polyacrylamide gel to be dried according to the method of the present invention is not particularly limited as long as it can be used for electrophoresis. For example, it may be a polyacrylamide gel having an arbitrary concentration or density gradient ranging from about 2 to 50% by weight. The polyacrylamide gel may be that formed from a substituted or unsubstituted acrylamide and optionally one or more other monomers.

The polyhydroxy alcohol used in the method of the invention may be any alcohol having 2 or more hydroxy groups provided that the alcohol is not one having 3 or more vicinal hydroxy groups. Preferably the polyhydroxy alcohol has a ratio of carbon to hydroxy groups such that the polyhydroxy compound remains water soluble. More preferably, the polyhydroxy alcohol has no more than 6 hydroxy groups. For example, the polyhydroxy alcohol may be a diol, triol or tetraol. Particular examples of suitable polyhydroxy alcohols are alkyl diols and alkyl tetraols. Particular example of polyhydroxy alcohols include 1,2-ethane diol, 1,2-propane diol, 1,3propane diol 1,4-butane diol, 1,6 hexane diol, 1,2,6-trihydroxy hexane, trimethylol propane and pentaerythritol. The polyhydroxy alcohol may be a polyglycerol, which is formed by the self-condensation of glycerol. The ether linkage between the glycerol units in the polyglycerol may be 1, 2 or 1, 3.

Surprisingly, it has been found that polyhydroxy alcohols in accordance with the present invention can be used in the method of the invention as an aqueous solution, without the need for an additional solvent. Not having to use additional solvents has obvious advantages in terms of environmental and safety issues. Although not required, a solvent other than water may be included in the aqueous solution. The other solvent may be any solvent used in polyacrylamide gel electrophoresis. The solvent may be such that it alters the rate of drying of the gel. The other solvent may be a water-soluble and highly volatile organic solvent. Examples of such organic solvents include C1–C4 alcohols such as methanol, ethanol, 1-propanol, 2-propanol, and butanol, as well as solvents such as acetone, tetrahydrofuran, acetonitrile, dimethyl formamide and dimethylsulfoxide. In the present invention, methanol, ethanol, 1-propanol, and 2-propanol are preferred. The organic solvents may be used singly or in combination of two or more. It is preferred that the organic solvents be present in amounts of 0.1–80% by weight, and more preferably 1–50% by weight, in the aforementioned aqueous solution.

The polyhydroxy alcohol may be present in an amount ranging from about 0.1% to about 20% of the aqueous solution. The actual concentration of the polyhydroxy alcohol in the aqueous solution depends on the particular polyhydroxy alcohol used Ed the nature of the solveuts used in the solution.

The aqueous solution containing the polyhydroxy alcohol may include other components conventionally used in gel drying solutions. For example, the aqueous solution may contain one or more viscosity control agents, for example, a water soluble polymer.

In the method of the present invention, the solution component contained in a polyacrylamide gel following electrophoresis may be replaced by the aqueous solution of the polyhydroxy alcohol by immersing the gel in the aqueous solution for at least 1 minute end preferably for 10 minutes to 24 hours. When the aqueous solution is stirred or shaken, the time required for replacement of the components in a polyacrylamide gel can be reduced. The volume of the aqueous solution is preferably at least equivalent to that of the polyacrylamide gel to dry, and particularly preferably at least 4 times that of the gel. The polyacrylamide gel used for electrophoresis is preferably washed with water or the like before being immersed in the aqueous solution contain the polyhydroxy alcohol.

The drying step of the method of the present invention may be according to any of the prior art drying methods described above The drying method used in the method of the present invention may be air drying or vacuum assisted drying. Preferably the gel is dried by placing the gel, which has been treated with an aqueous solution in accordance with the present invention, between two sheets or films at least one of which is a porous hydrophilic film. The porous hydrophilic sheet or film may be a cellophane film. Most preferably, the gel is dried by sandwiching it between two cellophane films held between two drying frames. Drying frames are well known. The drying frames may simply be rectangular frames made of a suitable substance, for example, perspax. The drying frames may be a more complex arrangement, for example, that described in U.S. Pat. No. 5,572,802, the disclosure of which is incorporated herein by reference. The two frames may be clamped together by using one or more clamps, for example, bulldog clips.

Throughout this specification the word comprised or variations such as "comprises" or "comprising", will be understood to imply the inclusion of a stated element, integer or step, or group of elements, integers or steps, but not the exclusion of any other element, integer or step, or group of elements, integers or steps.

In order that the present invention may be more readily understood, the following non-limiting embodiments are provided.

BRIEF DESCRIPTION OF THE DRAWINGS

FIG. 2 shows images of gradient 4–20% polyacrylamide gels that have been dried using solutions containing equivalent amounts of glycerol ($2(a)$) in accordance with the prior art and 1,2-ethane diol ($2(b)$), 1,2-propane diol ($2(c)$), 1,3-propane diol ($2(d)$), 1,4-butane diol ($2(e)$), 1,6 hexane diol ($2(f)$, 1,2,6-trihydroxy hexane ($2(g)$), trimethylol propane ($2(h)$) and pentaerythritol ($2(i)$) respectively, in accordance with the present invention.

FIG. 3 shows images of gels dried using an aqueous solution containing 1,2-ethane diol using R-250 coomassie blue stain ($3(a)$), and silver stain ($3(b)$) and 6% homogenous gel ($3(c)$) and 8% homogenous gel ($3(d)$)

FIG. 4 shows ea image of a 4–20% polyacrylamide gel dried in an aqueous solution containing 4% 1,2-ethane diol with no organic solvent.

DETAILED DESCRIPTION OF EMBODIMENTS

Examples 1–8

Figure 1:
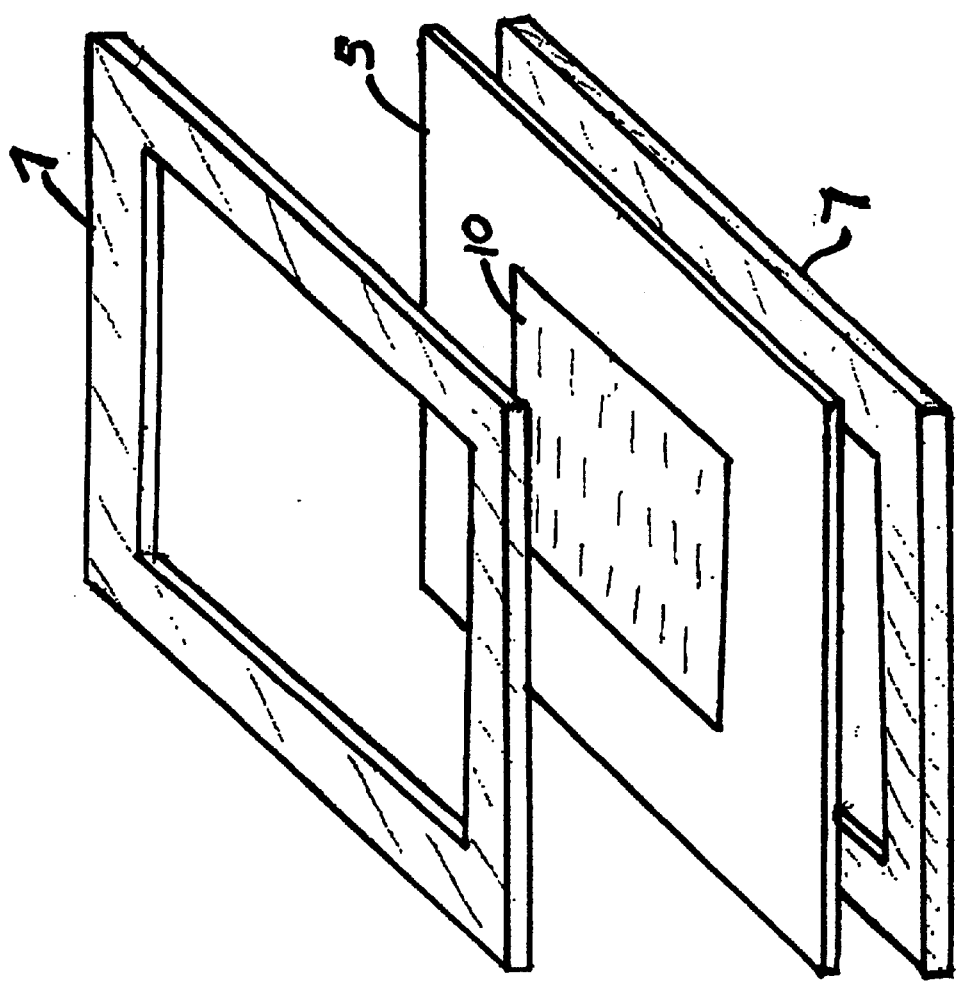
FIG. 1 is a schematic view of a drying frame arrangement for drying a polyacrylamide gel in accordance with the method of the present invention.

A polyacrylamide gel which was used under the following conditions for SDS-polyacrylamide gel electrophoresis (SDS-PAGE) was dried.
(1) Polyacrylamide gel:
  0.375M Tris-HCl buffer
  4–20% gradient gel
  Gel size: 80×100×1 mm
(2) Sample used for electrophoresis:
  Protein extracted from snow pea seed extract
  Broad range molecular weight marker
  A sample was prepared in accordance with the manufacturer's instructions, and was applied into each well in the gel in an amount of 5 µl.
(3) Buffer for electrophoresis:
  0.025M Tris—0.192M glycine+0.1% SDS
(4) Current:
  150 V Constant voltage, approximately 90 minutes.
(5) Staining and discolouration:
  A gel which had been for electrophoresis was shaken in a CBB staining liquid (GradiPure™) for at least 2 hours, after which the gel was transferred into a liquid for discolouration (6% acetic acid) The liquid for discolouration was changed as needed until proper staining results were obtained.
(6) Drying frame arrangement
  The drying frame arrangement used in the experiments is shown in FIG. 1 Electrophoresis gel 10, having been treated with a drying solution was sandwiched between two cellophane sheets 5. The sheets in turn a sandwiched between two perspex frames 7, which may be held together by bulldogs clips (not shown).
(7) Drying of a gel:
  After washing the discoloured gel using purified water, the gel was shaken in 50 ml of a drying solution containing 35% aqueous methanol solution and between 0.5 to 5% of polyhydroxy alcohol. A series of gradient 4–20% polyacrylamide gels were dried, each gel using an aqueous solution containing a polyhydroxy alcohol as set out in Table 1.

Subsequently, the gel was sandwiched between 2 transparent cellophane sheets which had been swollen in the drying solution and dried in the drying frame arrangement described above for at least 24 hours.

TABLE 1

| Experiment No | Polyhydroxy alcohol | Dried Gel FIG. |
| --- | --- | --- |
| 1 | 1,2-ethane diol | 2(b) |
| 2 | 1,2-propane diol | 2(c) |
| 3 | 1,3-propane diol | 2(d) |
| 4 | 1,4-butane diol | 2(e) |
| 5 | 1,6-hexane diol | 2(f) |
| 6 | 1,2,6-trihydroxy hexane | 2(g) |
| 7 | trimethylol propane | 2(h) |
| 8 | pentaerythritol | 2(i) |

As can be seen from the photocopies of the resultant dried gels shown in FIG. 2, all dried gels were clear and did not have any cracks.

Examples 9–13

The general procedure of the Example 1 is followed using a drying solution containing 4% 1,2-ethane diol. As shown in Table 2, Experiment 9 was carried out on a 4–20% gradient gel using R-250 coomassie blue stain and Experiment 10 with the same gradient gel using a silver stain. Drying experiments were carried out on a 6% homogenous gel (Experiment 11) and a 8% homogenous gel (Experiment 12). In each case the gels were clear and no cracking of the gel was observed.

Experiment 13 was carried out using a 4–20% gradient gel in an aqueous solution containing 4% 1,2-ethane diol with no methanol solvent. The aqueous solution produced a clear gel with no cracking of the gel.

TABLE 2

| | 1,2-ethane diol | | |
| --- | --- | --- | --- |
| Experiment No | Gel | stain | Dried Gel FIG. |
| 9 | 4–20% gradient gel | R-250 coomassie blue | 3(a) |
| 10 | " | silver | 3(b) |
| 11 | 6% homogenous gel | G-250 coomassie blue | 3(c) |
| 12 | 8% homogenous gel | G-250 coomassie blue | 3(d) |
| 13 | 4–20% gradient gel dried in aqueous solution containing 4% 1,2-ethane diol with no additional solvent. | G-250 coomassie blue | 4 |

COMPARATIVE EXAMPLE

The general procedure of the Example was repeated except that the solution for soaking a polyacrylamide gel described under item (7) in the Example was a 35% aqueous methanol solution containing 4% glycerol. A photocopy of the resultant dried gel is shown in FIG. 2(a). As a result, the resultant dry polyacrylamide gel was severely cracked. In contrast, the triol 1, 2,6-trihydroxy hexane showed no sign of cracking (see FIG. 2(f)) which results suggest that as long as the polyhydroxy alcohol used does not 3 or more hydroxy groups in a vicinal arrangement, cracking of the gel is avoided.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method for drying a polyacrylamide gel, the method comprising contacting the gel with an aqueous solution of a polyhydroxy alcohol other than a polyhydroxy alcohol having at least 3 vicinal hydroxy groups and drying the gel.

2. A method according to claim 1 wherein the polyhydroxy alcohol has a carbon to hydroxy group ratio such that the polyhydroxy alcohol is water soluble.

3. A method according to claim 2 wherein the polyhydroxy alcohol has no greater that 6 hydroxyl groups.

4. A method according to claim 1 wherein the polyhydroxy alcohol is selected from the group consisting of diols, triols and tetraols.

5. A method according to claim 1 wherein the polyhydroxy alcohol is selected from the group consisting of 1,2-ethane diol, 1,2-propane diol, 1,3-propane diol, 1,4-butane diol, 1,6 hexane diol, 1,2,6-trihydroxy hexane, trimethylol propane and pentaerythritol.

6. A method according to claim 1 wherein the polyhydroxy alcohol is polyglycerol.

7. A method according to claim 1 wherein the aqueous solution contains a solvent other than water.

8. A method according to claim 7 wherein the solvent is selected from the group consisting of a C1–C4 alcohol, acetone, tetrahydrofuran, acetonitrile, dimethyl formamide and dimethylsulfoxide.

9. A method according to claim 1 wherein the polyacrylamide gel is formed from a substituted or unsubstituted acrylamide monomer and optionally at least one other monomer.

10. A method according to claim 1 wherein the polyacrylamide gel is an homogeneous gel.

11. A method according to claim 1 wherein the polyacrylamide gel is a gradient gel.

12. A method according to claim 1 wherein the drying step is carried out using air drying or vacuum assisted dying.

13. A method according to claim 12 whereon the gel is dried by placing the gel between two sheets or films, at least one of which is a porous hydophilic film.

14. A method according to claim 13 wherein one or both porous hydrophilic films is a cellophane film.

15. A method according to claim 14 wherein the gel is sandwiched between two cellophane films which in turn are located between two drying frames.

16. A method according to claim 1 wherein the polyhydroxy alcohol is 1,2 ethane diol.

17. A method according to claim 1 wherein the aqueous solution contains a viscosity control agent.

* * * * *